United States Patent [19]

Bradvica

[11] Patent Number: 5,537,841
[45] Date of Patent: Jul. 23, 1996

[54] EARLOBE SUPPORT PATCH FOR EARRINGS

[76] Inventor: Joann G. Bradvica, 930 E. Longden Ave., Arcadia, Calif. 91004

[21] Appl. No.: 422,719

[22] Filed: Apr. 14, 1995

[51] Int. Cl.$^6$ ....................................................... A44C 7/00
[52] U.S. Cl. .................................................. 63/12; 63/14.3
[58] Field of Search ............................... 63/12, 13, 14.3, 63/14 B, DIG. 1

[56] References Cited

U.S. PATENT DOCUMENTS

| | | | |
|---|---|---|---|
| 1,971,216 | 8/1934 | Gould | 63/14.3 |
| 4,067,341 | 1/1978 | Ivey. | |
| 4,089,189 | 5/1978 | Verducci. | |
| 4,630,452 | 12/1986 | Connelly | 63/12 |
| 4,974,430 | 12/1990 | Turner | 63/12 |
| 5,044,176 | 9/1991 | King | 63/12 |
| 5,081,853 | 1/1992 | Salyer | 63/12 |
| 5,375,433 | 12/1994 | Skalet | 63/12 |
| 5,444,994 | 8/1995 | Poortinga | 63/14.3 |

*Primary Examiner*—Flemming Saether
*Attorney, Agent, or Firm*—Skjerven, Morrill, MacPherson, Franklin & Friel; Brian D. Ogonowsky

[57] ABSTRACT

In a preferred embodiment of the invention, an earlobe support patch is adhesively fixed to the back of a wearer's earlobe to cover the earring hole in the earlobe. The earring post is then inserted through the hole and through the earlobe support patch. The earring post is then secured on the earlobe using a conventional earring backing. The downward weight of the earring is now supported in large part by the earlobe support patch, which is, in turn, supported by a large area of the earlobe. Thus, the earring hole is not pulled a substantial extent.

23 Claims, 1 Drawing Sheet

5,537,841

EARLOBE SUPPORT PATCH FOR EARRINGS

FIELD OF THE INVENTION

This invention relates to earrings and, in particular, to an earlobe support for pierced earrings.

BACKGROUND OF THE INVENTION

The full weight of pierced earrings is typically supported by the bottom edge of a hole formed in the wearer's earlobe. Medium to heavy pierced earrings, such as dangling or loop earrings, pull down on the hole in the wearer's earlobe so that the hole becomes a very unattractive vertical slit. This downward weight also distorts the shape of the earlobe and may even tear the skin of the earlobe. Similarly, an inadvertent pull on the earring may easily cause tearing of the earlobe.

What is needed is a way to reduce the stress on earring holes from the downward pull of pierced earrings.

SUMMARY OF THE INVENTION

In a preferred embodiment of the invention, an earlobe support patch is adhesively fixed to the back of a wearer's earlobe to cover the earring hole in the earlobe. The earring post is then inserted through the hole and pierces the earlobe support patch. The earring post is then secured on the earlobe using a conventional earring backing. The downward weight of the earring is now supported in large part by the earlobe support patch, which is, in turn, supported by a large area of the earlobe. Thus, the earring hole is not pulled a substantial extent.

In one embodiment, the earlobe support patch is made of a fabric which may be easily pierced by the earring post. In another embodiment, the earlobe support patch is formed of a fabric, a plastic, or other material which has a hole already formed in the patch for supporting the earring post. The earlobe support patch may be made flesh colored or clear.

DETAILED DESCRIPTION OF THE PREFERRED EMBODIMENTS

Figure 1:
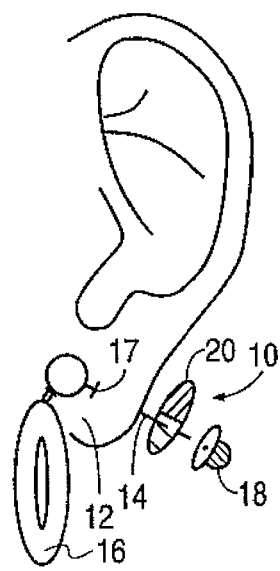
FIG. 1 is a view of the front of a person's pierced ear and an exploded view of the earlobe support patch, an earring, and an earring post for being inserted through the earlobe hole and through the earlobe support patch.

FIG. 1 illustrates the application of the preferred earlobe support patch 10 to the back of a wearer's earlobe 12 and the insertion of an earring post 14 of an earring 16 through an earring hole 17 and through the patch 10. FIG. 1 also illustrates a conventional earring backing 18 for being secured to post 14. The front of patch 10 has an adhesive portion 20.

Figure 2:
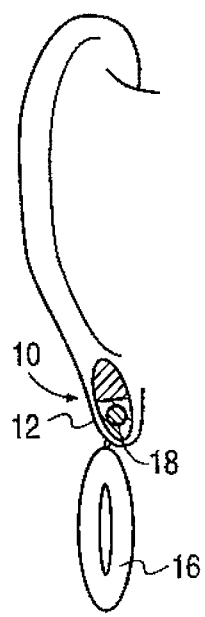
FIG. 2 is a view of the back of the person's ear with the earlobe support patch firmly secured to the back of the earlobe and the earring now secured through the earring hole and through the earlobe support patch.

FIG. 2 is a back view of the wearer's ear showing the patch 10 adhesively secured to the earlobe 12 via adhesive portion 20 and showing earring 16 being secured to both the earlobe 12 and to the patch 10 by operation of the post 14 and backing 18.

Figure 3:
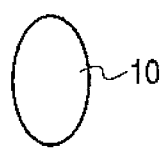
FIG. 3 is a back view of a preferred embodiment earlobe support patch.

FIG. 3 is a back view of patch 10. In one embodiment, patch 10 is made of a thin, densely-threaded fabric such as that conventionally used for medical cloth adhesive tape. Suitable fabric is commercially available. In one embodiment, the patch 10 is formed in an oval shape having a height of approximately ¾ inches and a width of approximately ⅜ inches. However, patch 10 may be formed to have virtually any shape and dimensions. A practical range of height and width dimensions for any shape is between approximately ¼ inch to one inch.

Figure 7:
FIGS. 7, 8, and 9 illustrate embodiments where the earlobe support patch is adhesively secured to the earlobe below the earring hole.
Figure 8:
Figure 9:
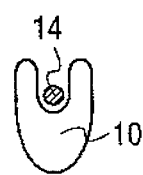

In another embodiment, patch 10, instead of an oval, has a circular shape, a rectangular shape, or an irregular shape such as shown in FIGS. 7–9.

Figure 4:
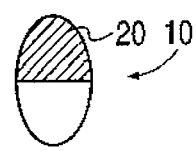
FIG. 4 is a front view of the preferred embodiment earlobe support patch showing the adhesive portion of the patch.

FIG. 4 illustrates a front surface of the patch 10 showing the adhesive portion 20. A suitable adhesive may be that used in medical cloth adhesive tape or any other suitable non-allergenic adhesive. Such an adhesive may be deposited on the back of patch 10 in liquid form in a conventional manner. Even a double-sided tape may form a suitable adhesive.

Although the adhesive portion 20 may cover any portion of the back of patch 10, including the entire back surface, it has been found that forming the adhesive on the top portion of the patch 10 is preferred to avoid any adhesive sticking to the post 14. The invention, however, is intended to encompass all those embodiments which include adhesive on any area of the back surface of the patch 10.

Referring back to FIG. 1, to use patch 10, the earlobe 12 is cleaned, and the adhesive portion 20 is pressed on the back of the earlobe 12 so that the portion of the patch 10 without the adhesive overlies the hole 17 in the earlobe 12. The user then pushes the post 14 of the earring 16 through the earring hole 17 and through the patch 10, then secures the post 14 in place with a conventional backing 18. The weight of the earring 16 is now largely supported by the patch 10 and, in turn, supported by the earlobe via the adhesive. This greatly reduces the stress on the earring hole 17 to the point that the earring hole 17 is not noticeably pulled by the weight of earring 16.

In a preferred embodiment, patch 10 is formed in a variety of shades to match the user's particular skin color.

Figure 5:
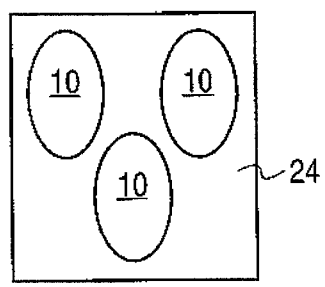
FIG. 5 illustrates how a plurality of earlobe support patches may be secured to a wax backing.

FIG. 5 illustrates one method of dispensing patches 10 by securing patches 10 to a wax backing 24. The user simply peels the patches 10 off the wax backing 24 as needed and may either reuse patches 10 or dispose of the patches 10 after a single use. In another embodiment, a wax backing may be formed to just cover the adhesive portion 20 of the patch 10 and may be simply peeled off the front of the patch 10 when the patch 10 is to be used.

Figure 6:
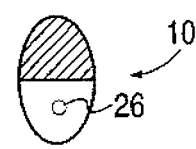
FIG. 6 illustrates another embodiment of the earlobe support patch being formed with a hole.

FIG. 6 illustrates the back of another embodiment of patch 10, which is formed of a clear plastic or other suitable material having a hole 26 already formed in it. A preformed hole 26 may be desirable, since earring posts 14 are typically dull at their ends, and it may be difficult to pierce the fabric type of patch 10 illustrated in FIG. 3. Hole 26 may be any shape, such as a rectangle or a slit.

FIGS. 7, 8, and 9 illustrate embodiments of earlobe support patches 10 which are adhesively secured to the earlobe below the earring hole and which support the downward force of the earring post 14. The front surface of the patches 10 of FIGS. 7–9 is coated with a suitable adhesive. These patches 10 may be formed of a fabric, a plastic, or other suitable material.

While particular embodiments of the present invention have been shown and described, it will be obvious to those skilled in the art that changes and modifications may be made without departing from this invention in its broader aspects and, therefore, the appended claims are to encompass within their scope all such changes and modifications as fall within the true spirit and scope of this invention.

What is claimed is:

1. A method for supporting an earring on a wearer's earlobe comprising the steps of:

providing a patch having an adhesive on at least a portion of a first side of said patch, said patch being of a size such that it may be affixed to a back of a wearer's earlobe without extending around, under, or below said earlobe;

adhesively affixing said first side of said patch to said back of said earlobe so that said patch does not extend around, under, or below said earlobe and so that said patch covers a back of an earring hole in said earlobe with at least a portion of said patch residing below said earring hole; and after said patch is affixed to said earlobe, inserting a support portion of an earring through a front of said earring hole and, upon further insertion, pushing said support portion against said patch with sufficient force so as to pierce said patch, such that the weight of said earring is then supported, at least partially, by said patch adhesively secured to said back of said earlobe.

2. The method of claim 1 wherein said patch comprises a fabric.

3. The method of claim 1 wherein said patch comprises a plastic material.

4. The method of claim 1 further comprising the steps of peeling a protective backing from an adhesive surface of said patch so as to expose said adhesive surface of said patch, and then securing said adhesive surface to said back of said earlobe.

5. The method of claim 1 wherein said patch has a substantially constant thickness along its entire surface.

6. The method of claim 1 wherein said support portion of said earring comprises a substantially straight earring post.

7. The method of claim 1 wherein said first side of said patch has an adhesive on only a portion of said first side.

8. The method of claim 1 wherein said first side of said patch is totally covered with an adhesive.

9. The method of claim 1 wherein said first side of said patch has an adhesive on only an upper portion of said first side, wherein said upper function is affixed to back of said earlobe above said earring hole.

10. The method of claim 1 wherein said patch is oval shaped.

11. A method for supporting an earring on a wearer's earlobe comprising the steps of:

providing an earring having a support portion for insertion through an earring hole in an earlobe;

providing a piece of material formed as a patch, said patch having an adhesive on only a first portion of a first side of said patch;

affixing said first portion of said patch to a back of a person's earlobe above an earring hole in said earlobe, a second portion of said patch being located below said earlobe hole, said patch being of a size such that it is affixed to said back of said earlobe without extending around, under, or below said earlobe; and inserting said support portion of said earring through said earring hole in said earlobe such that said patch supports, at least partially, the weight of said earring.

12. The method of claim 11 wherein said patch is formed of a fabric.

13. The method of claim 11 wherein said patch is formed of a plastic.

14. The method of claim 11 wherein said support portion for said earring is a substantially straight earring post.

15. The method of claim 11 wherein said patch has a preformed hole in it which is aligned with said earring hole during said step of affixing said first portion of said patch to said back of said earlobe.

16. The method of claim 11 wherein said support portion of said earring pierces said patch, during said step of inserting said support portion through said earring hole, to form a hole in said patch.

17. A method for supporting an earring on a wearer's earlobe comprising the steps of:

providing an earring having a support portion for inserting through an earring hole in an earlobe;

providing a piece of material formed as a patch, said patch having an adhesive on a first side of said patch, said patch having a first edge;

affixing said first side of said patch to a back of a person's earlobe so that said first edge is located directly below an earring hole in said earlobe, said patch being of a size such that it is affixed to said back of said earlobe without extending around, under, or below said earlobe; and inserting said support portion of said earring through said earring hole in said earlobe such that said first edge of said patch supports, at least partially, the weight of said earring.

18. The method of claim 17 wherein said patch is formed of a fabric.

19. The method of claim 17 wherein said patch is formed of a plastic.

20. The method of claim 17 wherein said support portion for said earring is a substantially straight earring post.

21. The method of claim 17 wherein said first edge of said patch is substantially straight.

22. The method of claim 17 wherein said first edge of said patch has a U-shape.

23. The method of claim 22 wherein a middle portion of said first edge having a U-shape is below said earring hole after said step of affixing, and opposing sides of said first edge extend along opposite sides of said earring hole.

* * * * *